US008486384B2

(12) United States Patent
Shen et al.

(10) Patent No.: US 8,486,384 B2
(45) Date of Patent: Jul. 16, 2013

(54) LIPIDIZED INTERFERON AND METHODS OF TREATING VIRAL HEPATITIS

(75) Inventors: Wei-Chiang Shen, San Marino, CA (US); Liyun Yuan, Pasadena, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 12/446,487

(22) PCT Filed: Oct. 29, 2007

(86) PCT No.: PCT/US2007/022770
§ 371 (c)(1),
(2), (4) Date: Jun. 8, 2009

(87) PCT Pub. No.: WO2008/057298
PCT Pub. Date: May 15, 2008

(65) Prior Publication Data
US 2010/0303761 A1    Dec. 2, 2010

Related U.S. Application Data

(60) Provisional application No. 60/863,263, filed on Oct. 27, 2006.

(51) Int. Cl.
*A61K 38/21* (2006.01)
*A61K 38/00* (2006.01)
*C07K 14/56* (2006.01)

(52) U.S. Cl.
USPC ............................ 424/85.7; 530/351; 514/1.1

(58) Field of Classification Search
None
See application file for complete search history.

(56) References Cited

U.S. PATENT DOCUMENTS

| | | | |
|---|---|---|---|
| 4,618,492 A | 10/1986 | Blattler et al. | |
| 4,764,368 A | 8/1988 | Blattler et al. | |
| 5,144,011 A | 9/1992 | Shen et al. | |
| 5,505,931 A | 4/1996 | Pribish | |
| 5,563,250 A | 10/1996 | Hylarides et al. | |
| 5,907,030 A | 5/1999 | Shen et al. | |
| 6,093,692 A * | 7/2000 | Shen et al. | 514/1.1 |
| 6,225,445 B1 * | 5/2001 | Shen et al. | 530/350 |
| 6,590,071 B1 | 7/2003 | Shen et al. | |
| 2004/0258663 A1 | 12/2004 | Quay et al. | |

FOREIGN PATENT DOCUMENTS

| | | |
|---|---|---|
| AU | 764035 | 11/2003 |
| CN | 1235594 A | 11/1999 |
| EP | 0183 503 | 6/1986 |
| EP | 0495 265 | 7/1992 |
| IL | 143578 | 10/2006 |
| WO | WO 96/22773 A1 | 8/1996 |
| WO | WO 98/13007 A2 | 4/1998 |
| WO | WO 9958152 | 11/1999 |
| WO | WO0034236 | 6/2000 |
| WO | WO2008057298 | 5/2008 |

OTHER PUBLICATIONS

Basu, J., Protein palmitoylation and dynamic modulation of protein function. Current Science, 2004, vol. 87, No. 2, p. 212-217.*
Kumar, T.R.S., et al., "Novel Delivery Technologies for Protein and Peptide Therapeutics," *Curr. Pharm. Biotechnol.* 7:261-276, Bentham Science Publishers Ltd. (2006).
Wan, L., and Chang, T.W., "Site-Specific Lipophilic Modification of Interferon-α," *J. Protein Chem 21*:371-380, Plenum Publishing Corporation (2002).
Wang, Y.-S., et al., "Structural and biological characterization of pegylated recombinant interferon alpha-2b and its therapeutic implications," *Adv. Drug Deliv. Rev. 54*:547-570, Elsevier Science B.V. (2002).
International Search Report for International Application No. PCT/US2007/22770, United States Patent and Trademark Office, Alexandria, Virginia 22313, mailed on Apr. 25, 2008.
Zhao, C.-Y., et al., "Changes of immunoregulatory cytokines in patients with chronic viral hepatitis pre- and post-treament with interferon-alfa," *Chinese Journal of Immunology 17*:327-330 (2001).
ISR-IPRP-WO from PCT/US1999/029119, dated Jun. 4, 2000.
OA in CN200780039858, dated Nov. 12, 2010.
OA in CN200780039858, dated Nov. 30, 2011.
Kayser, M. et. al., Can J Chem 1993 vol. 71, pp. 1010-1012.
EP Extended Search Report, dated Nov. 29, 2011.
Yuan, et al. "Reversible Lipidization Prolongs the Pharmacological Effect, Plasma Duration, and Liver Retention of Octreotide," Pharmaceutical Research, vol. 22, No. 2, Feb. 2005 pp. 220-227.
Notice of Reasons for Rejection in Japan, Oct. 22, 2012.

* cited by examiner

*Primary Examiner* — Robert Landsman
*Assistant Examiner* — Bruce D Hissong
(74) *Attorney, Agent, or Firm* — Hema Vakharia-Rao; Nixon Peabody LLP

(57) ABSTRACT

The present invention is directed to methods and compositions useful in increasing in mammals the absorption and retention of polypeptides. The invention provides lipid-conjugated interferon having increased liver uptake and increased plasma half-life.

6 Claims, 9 Drawing Sheets

SEQUENCE LISTING

```
<160> NUMBER OF SEQ ID NOS: 3

<210> SEQ ID NO 1
<211> LENGTH: 12
<212> TYPE: PRT
<213> ORGANISM: Artificial Sequence
<220> FEATURE:
<223> OTHER INFORMATION: Synthetic IFN with a palmitoyl cysteine
<220> FEATURE:
<221> NAME/KEY: LIPID
<222> LOCATION: (1)..(1)
<223> OTHER INFORMATION: PALMITATE

<400> SEQUENCE: 1

Cys Asp Leu Pro Gln Thr His Ser Leu Gly Ser Arg
1               5                   10

<210> SEQ ID NO 2
<211> LENGTH: 28
<212> TYPE: PRT
<213> ORGANISM: Artificial Sequence
<220> FEATURE:
```

```
<223> OTHER INFORMATION: Synthetic IFN with a palmitoyl cysteine
<220> FEATURE:
<221> NAME/KEY: LIPID
<222> LOCATION: (7)..(7)
<223> OTHER INFORMATION: PALMITATE

<400> SEQUENCE: 2

Arg Ile Ser Leu Phe Ser Cys Leu Lys Asp Arg His Asp Phe Gly Phe
1               5                  10                 15

Pro Gln Glu Glu Phe Gly Asn Gln Phe Gln Lys Ala
            20                  25

<210> SEQ ID NO 3
<211> LENGTH: 13
<212> TYPE: PRT
<213> ORGANISM: Artificial Sequence
<220> FEATURE:
<223> OTHER INFORMATION: Synthetic IFN with a palmitoyl cysteine
<220> FEATURE:
<221> NAME/KEY: LIPID
<222> LOCATION: (6)..(6)
<223> OTHER INFORMATION: PALMITATE

<400> SEQUENCE: 3

Lys Lys Tyr Ser Pro Cys Ala Trp Glu Val Val Arg Ala
1               5                  10
```

LIPIDIZED INTERFERON AND METHODS OF TREATING VIRAL HEPATITIS

BACKGROUND OF THE INVENTION

1. Field of the Invention

The present invention relates generally to the fields of biology and medicine. The present invention is directed to methods and compositions useful in increasing in mammals the absorption and retention of polypeptides. More particularly, the invention is directed to lipid-conjugated interferon having increased liver uptake and increased plasma half-life.

2. Background Art

Interferon-α (IFN-α) is considered the most effective antiviral agent for chronic viral hepatitis that currently affects approximately 800 million people worldwide (Hoofnagle et al., *N. Engl. J. Med.* 336:347 (1997)). However, the short half-life and lack of liver-specific affinity hamper the IFN-α response. A sustained response is achieved in only one-third of patients with chronic hepatitis B and in only one-fifth of patients with chronic hepatitis C (Davis et al., *N. Engl. J. Med.* 321:1501 (1989); Poynard et al., *Hepatology* 24:778 (1996)).

Pegylation is most commonly used to modify IFN-α. Pegylated IFN-α, e.g., PEG-INTRON, was thus developed to prolong its half-life. Nevertheless, pegylation results in a heterogeneous species (Wang et al., *Adv. Drug Delivery Rev.* 54:547 (2002)). For PEG-INTRON, a nonselective, succinimidyl carbonate chemistry was used and consequently produced a mixture of pegylated forms: polyethylene glycol (PEG) with an average molecular weight of 12,000 Daltons is attached to the amine groups of at least 14 amino acid residues of IFN-α by covalent linkages (Wang et al., *Biochemistry* 39:10634 (2000)). Although the serum half-life was increased in pegylated IFNs with increased molecular weights of PEGs, the in vitro potency was significantly reduced by more than 75%. The increased hydrophilicity and bulkiness accordingly reduces the affinity of IFN-α for the liver.

BRIEF SUMMARY OF THE INVENTION

The present invention relates to lipid conjugated polypeptides, e.g., therapeutic polypeptides. The modified polypeptides exhibit increased plasma half-life and increased liver uptake, thereby enhancing the therapeutic potential of the polypeptide.

One embodiment of the invention relates to methods of increasing the liver uptake of a polypeptide upon administration to a subject, comprising conjugating the polypeptide with a lipid.

Another embodiment of the invention relates to methods of increasing the plasma half-life of a polypeptide upon administration to a subject, comprising conjugating the polypeptide with a lipid.

The invention further relates to methods of treating a liver disease in a subject, comprising administering to said subject a lipid conjugated therapeutic polypeptide.

In a further embodiment, the invention relates to a lipid conjugated polypeptide, wherein the polypeptide is a therapeutic polypeptide In an additional embodiment, the invention relates to pharmaceutical compositions comprising a lipid conjugated polypeptide.

In one embodiment, the protein is therapeutic for a liver disease, e.g., hepatitis. In one embodiment, the polypeptide is an interferon, e.g., interferon-α. In a further embodiment, the lipid is palmitoyl cysteine.

In one embodiment, the lipid is conjugated to the polypeptide through a reversible linkage, e.g., through modification of disulfide bonds in the polypeptide.

BRIEF DESCRIPTION OF THE DRAWINGS/FIGURES

The invention may be better understood with reference to the accompanying drawings.

DETAILED DESCRIPTION OF THE INVENTION

Figure 1A:
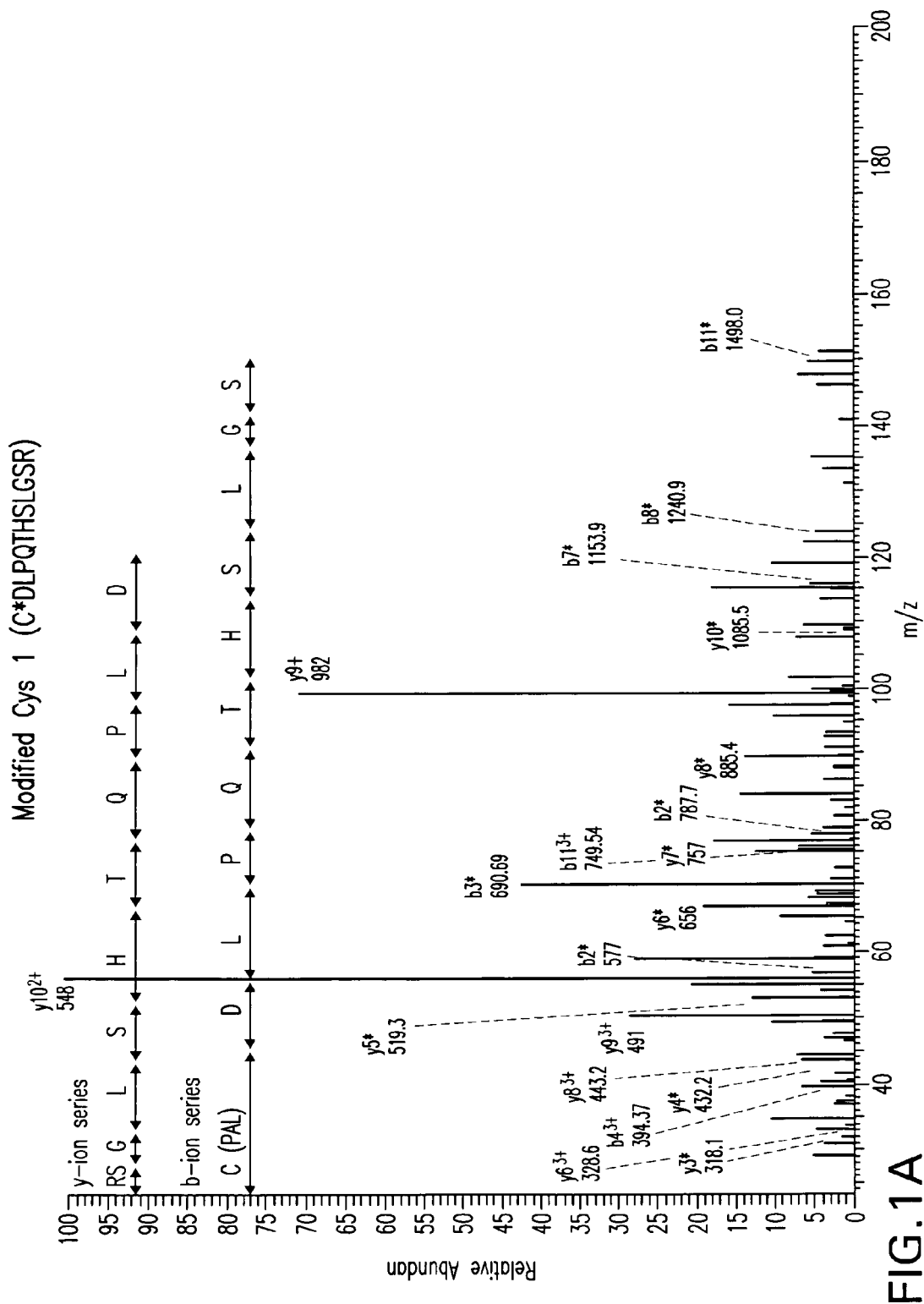
FIGS. 1A-1C are graphs of LC-MS spectra illustrating that palmitoyl cysteines are conjugated to IFN via disulfide bonds at the positions of Cys 1, Cys 29 and Cys 138 (SEQ ID NOS:1-3).

The invention relates to lipid conjugated polypeptides having increased plasma half-life and liver uptake and the use of the modified polypeptides for treatment of disease, e.g., liver disease.

The present invention may be practiced with any polypeptide, e.g., a therapeutic polypeptide. For purposes of the present invention, the term "polypeptide" refers to amino acid chains comprising three or more amino acids. The polypeptides may be isolated from natural sources or prepared by means well known in the art, such as recombinant DNA technology or solid-state synthesis. It is contemplated that the polypeptides used in accordance with the present invention may comprise only naturally-occurring L-amino acids, combinations of L-amino acids and other amino acids (including D-amino acids and modified amino acids), or only amino acids other than L-amino acids. In one embodiment of the invention, a lipid conjugate is formed through at least one reactive thiol group on the polypeptide. In many cases, the polypeptide contains cysteine residues (an amino acid comprising a thiol group). A polypeptide which does not contain a thiol group may be modified by procedures well known to those working in the field; in particular, well known thiolating agents (e.g., N-succinimidyl-3-(2-pyridyldithio)propionate (SPDP) and 2-iminothiolane (Traut's reagent)) may be routinely employed for this purpose.

Examples of therapeutic polypeptides include, but are not limited to, immunoglobulins, erythropoietin, an interferon such as interferon-α, interferon-β, interferon-γ, alpha-1 proteinase inhibitor, angiogenin, antithrombin III, beta-acid decarboxylase, human growth hormone, bovine growth hormone, porcine growth hormone, human serum albumin, calf intestine alkaline phosphatase, cystic fibrosis transmembrane regulator, Factor VIII, Factor IX, Factor X, insulin, lactoferrin, tissue plasminogen activator, myelin basic protein, insulin, proinsulin, prolactin, hepatitis B antigen, immunoglobulin fragments (e.g., FABs), monoclonal antibody CTLA41 g, Tag 72 monoclonal antibody, Tag 72 single chain antigen binding protein, protein C, cytokines and their receptors, including, for instance tumor necrosis factors alpha and beta, their receptors and their derivatives; renin; growth hormone releasing factor; parathyroid hormone; thyroid stimulating hormone; lipoproteins; alpha-1-antitrypsin; follicle stimulating hormone; calcitonin; luteinizing hormone; glucagon; von Willebrand factor; atrial natriuretic factor; lung surfactant; urokinase; bombesin; thrombin; hemopoietic growth factor; enkephalinase; human macrophage inflammatory protein (MIP-1-alpha); a serum albumin such as mullerian-inhibiting substance; relaxin A-chain; relaxin B-chain; prorelaxin; mouse gonadotropin-associated peptide; beta-lactamase; DNase; inhibin; activin; vascular endothelial growth factor (VEGF); receptors for hormones or growth factors; integrin; protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-beta; platelet-derived growth factor (PDGF); fibroblast growth factor such as aFGF and bFGF; epidermal growth factor (EGF); transforming growth factor (TGF) such as TGF-α and TGF-β, including TGF-1, TGF-2, TGF-3, TGF-4, or TGF-5; insulin-like growth factor-I and -II (IGF-I and IGF-II); des(1-3)-IGF-I (brain IGF-I), insulin-like growth factor binding proteins; CD proteins such as CD-3, CD-4, CD-8, and CD-19; osteoinductive factors; immunotoxins; a bone morphogenetic protein (BMP); colony stimulating factors (CSFs), e.g., M-CSF, GM-CSF, and G-CSF; interleukins (ILs), e.g., IL-1 to IL-12; superoxide dismutase; T-cell receptors; surface membrane proteins; decay accelerating factor; viral antigen such as, for example, a portion of the AIDS envelope; transport proteins; homing receptors; addressins; regulatory proteins; antibodies; chimeric proteins, such as immunoadhesins, and fragments or fusions of any of the above-listed polypeptides. Nucleic acid and protein sequences for these proteins are available in public databases such as GenBank.

In one embodiment, the therapeutic polypeptide is therapeutic for a liver disease, thereby taking advantage of the enhanced liver uptake of the conjugated polypeptide. Examples of liver diseases include, without limitation, hepatitis (e.g., viral hepatitis), cirrhosis, liver cancer, steatosis, and alcoholic liver disease. Polypeptides that are therapeutic for a liver disease include, but are not limited to, an interferon such as interferon-α, interferon-β, or interferon-γ.

For purposes of the present invention, the term "lipid" refers to either a lipid group per se or a hydrocarbon-based group (in particular, one or more amino acids) comprising a lipid group. By the term "lipid group" is meant a hydrophobic substituent consisting of 4 to 26 carbon atoms, preferably 5 to 19 carbon atoms. Suitable lipid groups include, but are not limited to, the following: palmityl ($C_{15}H_{31}$); oleyl ($C_{15}H_{29}$); stearyl ($C_{17}H_{35}$); cholate; and deoxycholate.

The lipid may be conjugated to the polypeptide by any linkage means known in the art. (See, e.g., U.S. Pat. Nos. 5,907,030; 6,590,071). In one embodiment of the invention, the lipid is conjugated to the polypeptide through a reversible linkage. Mechanisms for reversible linkage include, without limitation, reduction of disulfide bonds, hydrolysis, and photolytic bond cleavage. (See for example, U.S. Pat. No. 5,505,931 and references cited therein). Published PCT Application Nos. WO 96/22773 and WO 98/13007 disclose the transcellular delivery and release of sulfhydryl-containing peptides and proteins. The cellular absorption of sulfhydryl-containing polypeptides can be increased by conjugation with a lipid through a disulfide linkage. The labile disulfide linkage is easily reduced, providing a mechanism for the release of the polypeptide from the lipid once inside the body. Hydrolysis-based delivery systems in which a polypeptide is conjugated with an organic acid incorporating a monoclonal antibody or other substrate for the targeting of specific cells are known. (See U.S. Pat. Nos. 4,764,368, 4,618,492, 5,505,931 and 5,563,250). After specific binding to the targeted cell, these conjugates deliver the polypeptide inside the cell where hydrolysis releases the free polypeptide inside the cell.

In one embodiment of the invention, the lipid conjugated polypeptide is interferon-α. In a further embodiment, the interferon-α is conjugated with palmitoyl cysteine, e.g., at least two, e.g., three or four molecules of palmitoyl cysteine. In one embodiment, the interferon-α is reversibly conjugated with palmitoyl cysteine, e.g., through the formation of disulfide bonds between one or more cysteine residues of interferon-α and the cysteine moiety of palmitoyl cysteine.

The present invention further relates to methods of treating a disease or condition in a subject by administering to the subject a lipid conjugated polypeptide of the invention. The term "treating" refers to the administration to subjects of a lipid conjugated polypeptide for purposes which can include prevention, amelioration, or cure of a disease or condition. The modified polypeptide may be administered to a subject using any technique known in the art for treatment of a disease or condition by delivery of a polypeptide. In one embodiment, the lipid conjugated polypeptide is present or administered as part of a pharmaceutical composition.

Pharmaceutical compositions for administration according to the present invention can comprise at least one lipid conjugated polypeptide according to the present invention in a pharmaceutically acceptable form optionally combined with a pharmaceutically acceptable carrier. These compositions can be administered by any means that achieve their intended purposes. For example, administration may be by oral, parenteral, subcutaneous, intravenous, intramuscular, intraperitoneal, transdermal, intrathecal, intracranial or intranasal routes. The dosage administered will be dependent on the age, health, and weight of the recipient, kind of concurrent treatment, if any, frequency of treatment, and the nature of the effect desired. Amounts and regimens for administration according to the present invention can be determined readily by those with ordinary skill in the art of clinical treatment.

The form of administration may also include emulsions, nanoparticles (e.g., solid lipid nanoparticles), liposomes, microspheres, microcapsules, aerosols, through inhalation, and transdermal dosage forms.

Suitable formulations for parenteral administration include aqueous solutions of the compounds in water-soluble form. In addition, suspensions of the compounds as appropriately oily injection suspensions may be administered. Suitable lipophilic solvents or vehicles include fatty oils, for example, sesame oil, or synthetic fatty acid esters, for example ethyl oleate or triglycerides. Aqueous injection suspensions may contain substances which increase the viscosity of the suspension including, for example, sodium carboxymethyl cellulose, sorbitol, and/or dextran. Optionally, aqueous solutions and/or suspensions may also contain stabilizers and/or buffers, such as borate buffer and the like.

Pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture, and processing the mixture of granules, after adding suitable auxiliaries, if desired or necessary, to obtain tablets or dragee cores.

Suitable excipients are, e.g., fillers such as saccharide, lactose, sucrose, mannitol or sorbitol; cellulose preparations and/or calcium phosphates, such as tricalcium phosphate or calcium hydrogen phosphate; as well as binders such as starch paste, using, for example, maize starch, wheat starch, rice starch, potato starch, gelatin, tagaranth, methyl cellulose, hydroxypropylmethylcellulose, sodium carboxymethylcellulose, and/or polyvinyl pyrrolidone. If desired, disintegrating agents can be added such as the above-mentioned starches and also carboxymethyl starch, cross-linked polyvinyl pyrrolidone, agar or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which, if desired, are resistant to gastric juices. For this purpose concentrated saccharide solutions can be used which can optionally contain gum arabic, talc, polyvinyl pyrrolidone, polyethylene glycol, and/or titanium dioxide, lacquer solutions and suitable organic solvents or solvent mixtures. In order to produce coatings resistant to gastric juices, solutions of suitable cellulose preparations such as acetyl cellulose phthalate or hydroxypropylmethyl cellulose phthalate are used. Coatings may also be provided to protect the lipid conjugated polypeptide of the present invention from premature exposure to an acidic environment. See U.S. Pat. Nos. 4,786,505 and 4,853,230 for methods of preparing dosage units with cores that are protected from gastric acid. Preferably, the core is neutral or basic.

Basic cores contain one or more alkaline reacting compounds such as those described in U.S. Pat. Nos. 4,786,505 and 4,853,230. Dystuffs or pigments can be added to the tablets or dragee coatings, for example, for identification in order to characterize combinations of active compound doses.

Other pharmaceutical preparations which can be used include, but are not limited to, oral push-fit capsules made of gelatin, rectal suppositories, inhalation formulations for oral and/or nasal administration, nasal or rectal creams or ointments optionally combined with a pharmaceutically acceptable carrier, penetration enhancer, excipient, and/or filler. Penetration enhancers suitable for use include cationic, anionic, amphoteric and neutral penetration enhancers such as benzalkonium chloride, chlorbutanol, AZONE and others known in the art.

The following examples are illustrative, but not limiting, of the methods of the present invention. Other suitable modifications and adaptations of the variety of conditions and parameters normally encountered in medical treatment and pharmaceutical science and which are obvious to those skilled in the art are within the spirit and scope of the invention.

Example 1

Synthesis of Palmitoylated Human Interferon Alpha (PAL-IFN)

Human IFN-α was reversibly lipidized by conjugating palmitoyl cysteine specifically to cysteinyl residues of IFN-α via disulfide bonds. Through this synthetic strategy, a homogenous, single-species conjugate was produced, PAL-IFN. More importantly, disulfide linkers in PAL-IFN will ensure the release of unmodified IFN-α upon the reduction inside the body, possibly in the liver (Shen et al., Peptide and Protein Drug Delivery, S. Frokjer, L. Christrup, P. Krogsgaard-Larsen, Eds. (Munksgaard, Copenhagen, 1998) pp. 397-408). As a result, the released IFN-α will locally circulate in the liver with a prolonged period, thereby enhancing the therapeutic potential for viral hepatitis. The pharmacokinetics, biodistribution, and in vivo biological activity among PAL-IFN and pegylated and unmodified IFN-α was compared, proving the potential of PAL-IFN as a novel modified IFN with improved delivery and liver-targeting properties.

Human Interferon-alpha (hIFN-α) was obtained from BioVision (Mountain View, Calif.). In the following descriptions and figures, IFN is designated as hIFN-α only. Fifty microgram (μg) IFN was dissolved into 200 μL of PBS containing 0.5% Chaps. Freshly prepared dithiothreitol (DTT) (8 μL, 1 mg/ml) was added to the solution to reduce the disulfide bonds of IFN. After 1-hour incubation at 37° C., 24 μL of N-palmitoyl cysteinyl 2-pyridyl disulfide (Pal-CPD) was added to the reaction mixture and the incubation was continued for another hour at room temperature.

HPLC analysis was used to monitor the whole reaction. HPLC was conducted on a Hewlett-Packard 1050 HPLC system (Avondale, Pa.) employing a 250×4.6 mm Phenomenex Jupiter C4 column (Torrance, Calif.). The mobile phases were 5% acetonitrile in 0.1% trifluoroacetic acid (A) and 95% acetonitrile in 0.1% trifluoroacetic acid (B). A gradient elution was programmed, starting at 10% B, increasing to 100% B in 15 min and staying at 100% B for an additional 5 min. The detection was made at 214 nm). With HPLC analysis, IFN was eluted at 10.98 min, and PAL-IFN conjugate was eluted as a single peak at 13.112 min.

Example 2

Characterization of PAL-IFN

Liquid Chromatography-Ion Trap Mass Spectrometry (LC-MS) was applied to characterize the modification of PAL-IFN. 10 μg of PAL-IFN was digested with freshly prepared 1% trypsin for 2 hours at 37° C., and the digestion was repeated for another 2 hours and then overnight by replenishing with fresh 1% trypsin. The tryptic digestion was stopped by adding 5% acetic acid. The sample was desalted using C18 spin columns.

Mass spectrometric analysis of PAL-IFN was performed using a Thermo Finnigan LCQ Deca XPPlus mass spectrometer with RP-LC implemented with an Ultra Plus II LC system (Micro-Tech Scientific, Brockville, Ontario) using a 150 mm×75 μm C-18 reverse-phase (RP) column (5 μm 300 Å particles) from Micro-Tech Scientific. Peptides were loaded onto a Michrom Bioresources peptide cap trap at 95% solvent A (2% acetonitrile, 0.1% formic acid) and 5% solvent B (95% acetonitrile, 0.1% formic acid) and then eluted with a linear gradient of 5-60% solvent B for 65 min and 60-90% solvent B for 10 min. Tandem MS/MS spectra were acquired with Xcalibur 1.2 software. A full MS scan was followed by three consecutive MS/MS scans of the top three ion peaks from the preceding full scan.

Dynamic exclusion was enabled such that after three occurrences of an ion within 1 min, the ion was placed on the exclusion list for 3 min. Other mass spectrometric data generation parameters were as follows: collision energy 35%, full scan MS mass range 400-1800 m/z, minimum MS signal $5\times10^4$ counts, minimum MS/MS signal $5\times10^3$ counts. The mass spectrometer was equipped with a nanospray ion source (Thermo Electron) using an uncoated 10 μm-ID SilicaTip™ PicoTip™ nanospray emitter (New Objective, Woburn, Mass.). The spray voltage of the mass spectrometer was 1.9 kV and the heated capillary temperature was 180° C.

The obtained MS Spectra was analyzed as follows. A Beta test version of Bioworks (Bioworks 3.1) on a nine node (2 cpu/node) cluster computer from Thermo Electron utilizing the SEQUEST algorithm was used to determine cross correlation scores between acquired spectra and a human interferon alpha protein database. To identify Cys-conjugated PAL peptides, a differential modification of +358.559 (molecular weight of PAL) was used. Other SEQUEST parameters included threshold: 1000; monoisotopic; enzyme: trypsin; charge state: auto. For peptide identification, spectra passing a threshold of cross-correlation vs. charge state (1.5 for +1 ions, 2.0 for +2 ions, 2.5 for +3 ions) were then inspected to verify that all major ions were identified. MS/MS spectra were also manually validated.

Figure 1B:
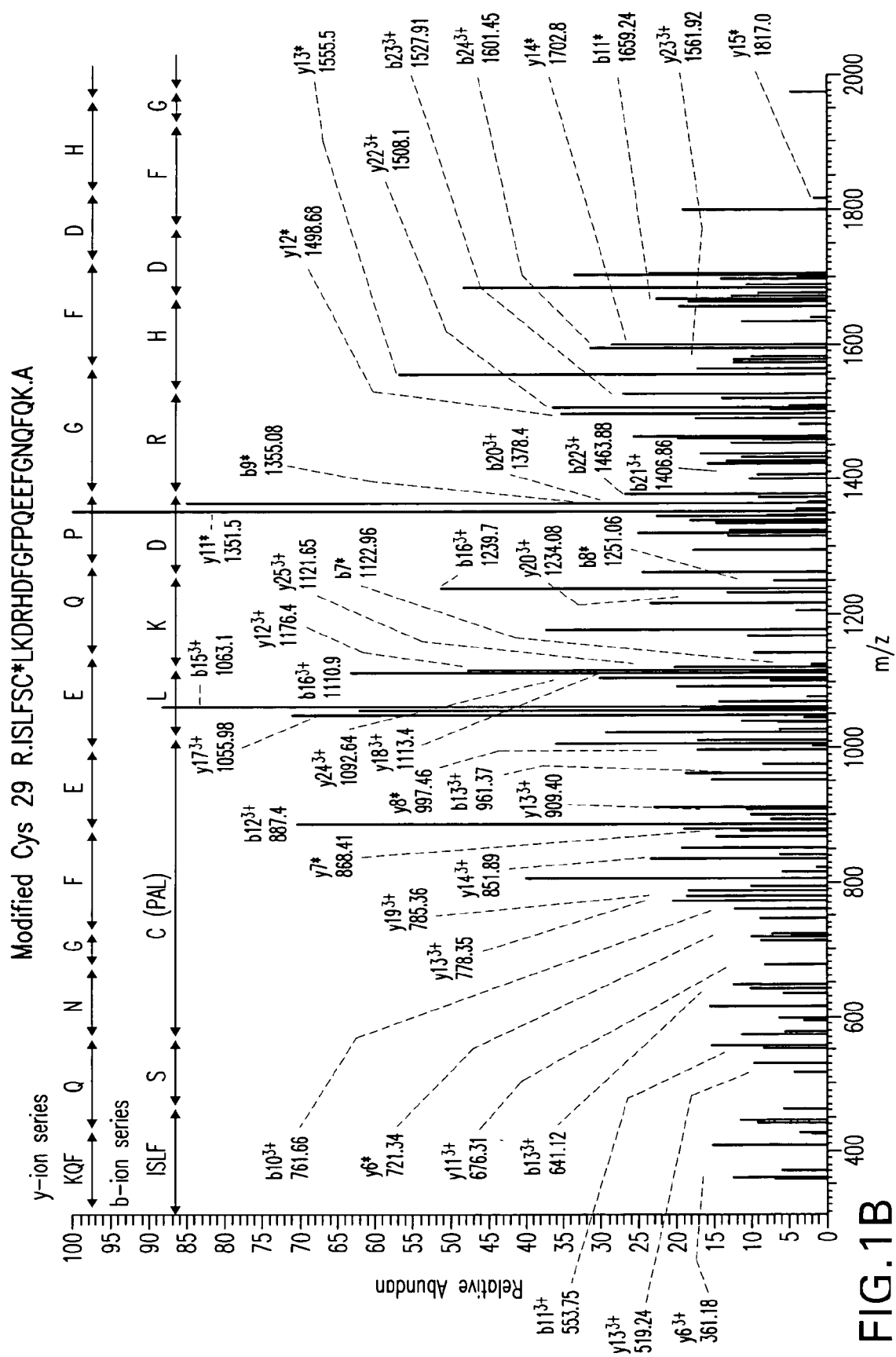
Figure 1C:
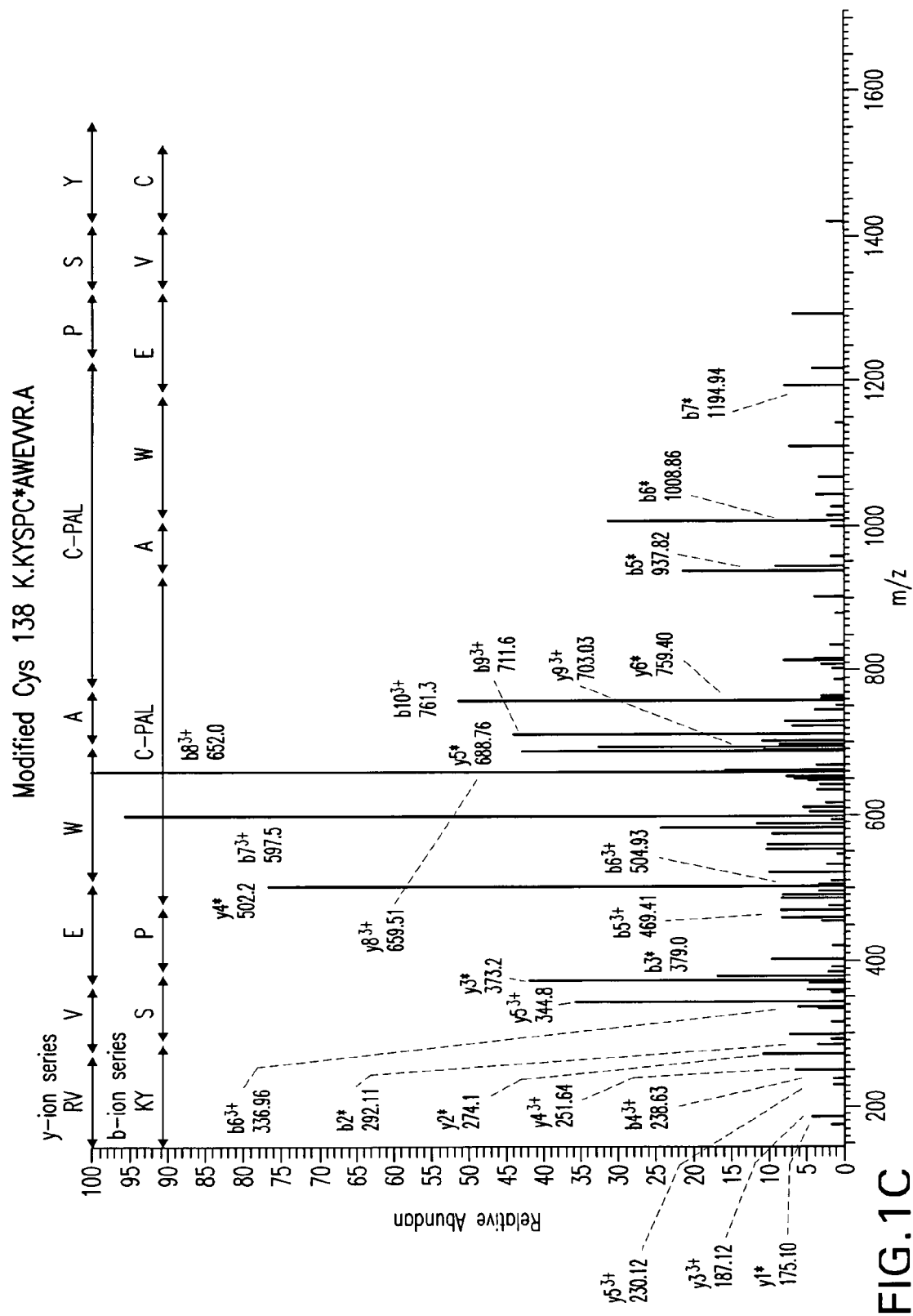

There are 4 cysteinyl residues to form two disulfide bonds (Cys1-Cys98; Cys29-Cys138) in IFN-α. The conjugation of palmitoyl cysteines to Cys1, Cys29 and Cys138 was identified with LC-MS. FIG. 1 shows the mass spectrum of Cys1 (A), Cys29 (B) and Cys138 (C) modifications. The tryptic fragment containing Cys98 was too large to be eluted out of the C-18 RP column in LC-MS. However, since the reduced cysteinyl residue is unstable in proteins, the modification of Cys1 (FIG. 1A) infers that Cys98 has also been lipidized.

Example 3

Plasma Level Versus Time Profile of Pal-IFN In Vivo

Male CF-1 mice weighing 27-30 g each, with free access to food and water prior to the experiments, were used for the animal experiments. $^{125}$I-PAL-IFN and $^{125}$I-IFN was administered to mice via the tail vein. At 5 min, 15 min, 30 min, 1, 2, 4, and 8 hours post injection, 3 animals from each experimental group were sacrificed and blood was collected from the heart. 200 μL of plasma was collected by centrifugation of blood for 10 min at 6,000 rpm. The intact proteins were precipitated with 20% ice-cold trichloroacetic acid, and the radioactivity in the precipitates was measured in a gamma counter.

Figure 2:
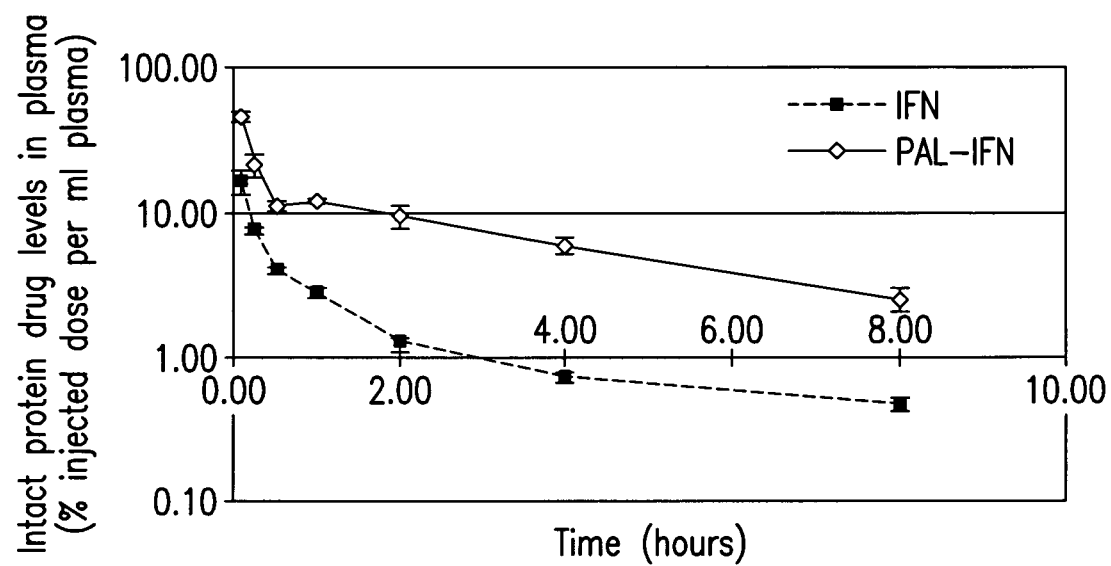
FIG. 2 is a graph which illustrates the plasma concentration versus time profile of PAL-IFN and IFN upon an intravenous administration to CF-1 mice.

FIG. 2 shows that the plasma concentration of PAL-IFN is significantly higher than that of IFN at each observed time point. The plasma PAL-IFN level displays both the distribution phase and the elimination phase, while IFN shows predominately the elimination phase. Calculated from the curves, the elimination half-life of PAL-IFN is 3.28 h, which is significantly prolonged, as compared to the half-life of non-modified IFN (0.73 h).

Example 4

Comparison of IFN, PAL-IFN and PEG-INTRON in Plasma Concentration and Liver Retention In Vivo The plasma level of PAL-IFN and its liver retention was further compared with those of IFN and PEG-INTRON. $^{125}$I-IFN, $^{125}$I-PAL-IFN and $^{125}$I-PEG-INTRON were intravenously injected to CF-1 mice. The mice were sacrificed at 15, 60 and 240 min post injection. The radioactivity in 200 μl of plasma and the whole liver of each mouse was measured.

Figure 3A:
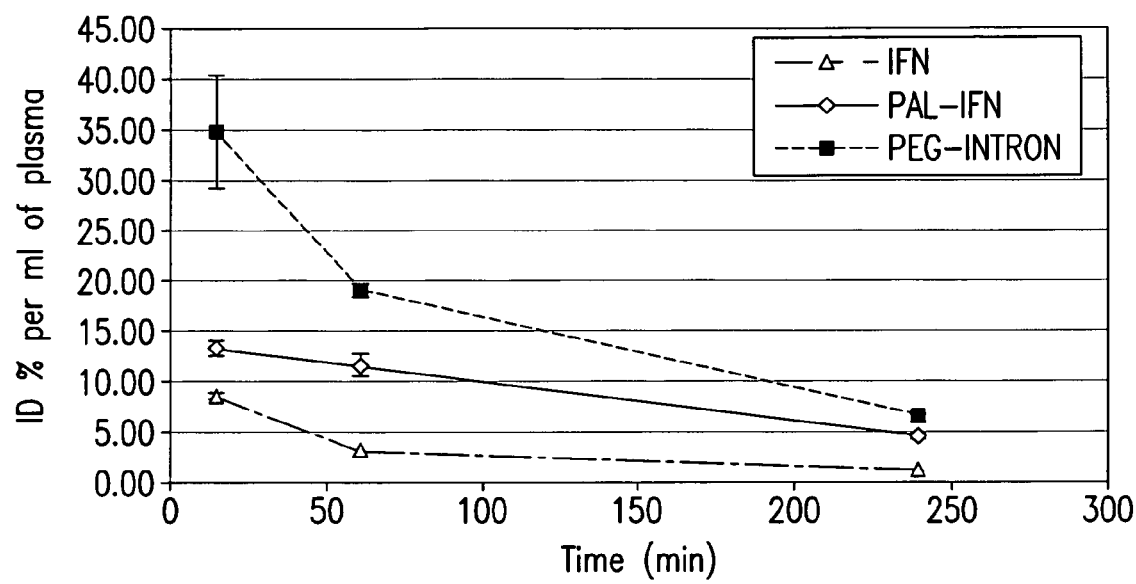
FIGS. 3A and 3B are a graph and bar graph, respectively, which illustrate the plasma levels and liver retention of PAL-IFN, IFN and PEG-INTRON at 15 min, 60 min and 240 min post iv injection to CF-1 mice.
Figure 3B:
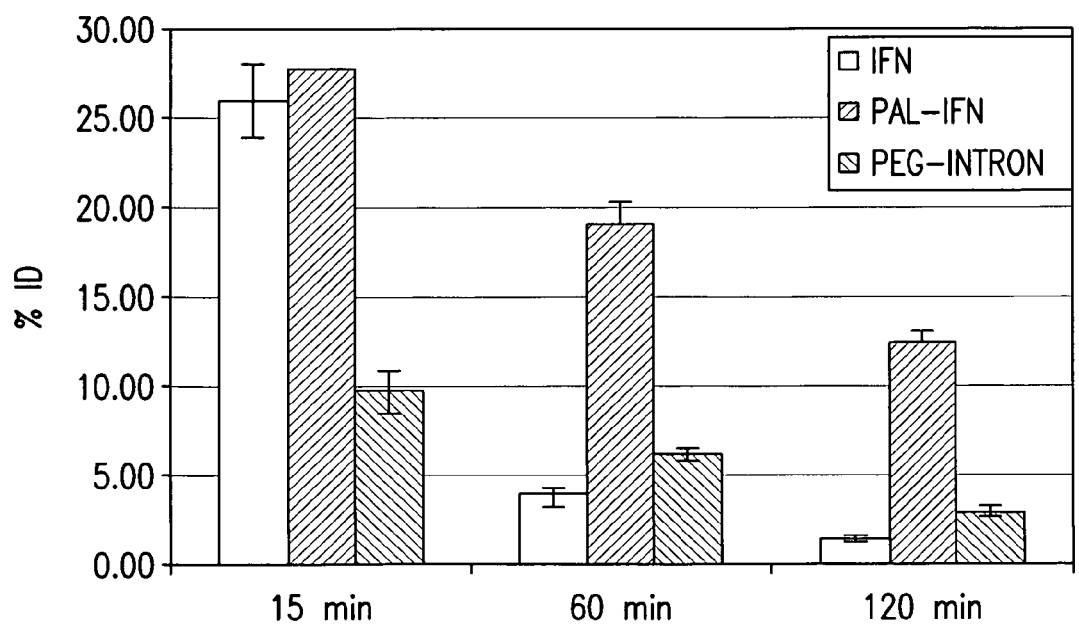

The elimination rate of PAL-IFN appeared to be slower than those of PEG-INTRON and IFN (FIG. 3A). Furthermore, PAL-IFN was retained in the liver with significantly higher concentration (FIG. 3B). As an example at 60 min post injection, 18.89% injected dose (ID) of PAL-IFN was absorbed to the liver, as compared to 3.66% ID of IFN and 5.92% ID of PEG-INTRON in the liver at the same time point.

Example 5

Cellular Uptake of PAL-IFN

Cellular uptake of PAL-IFN, IFN and PEG-INTRON was measured in both the Sg-PC2 cell line and primary cultured mouse hepatocytes.

Figure 4A:
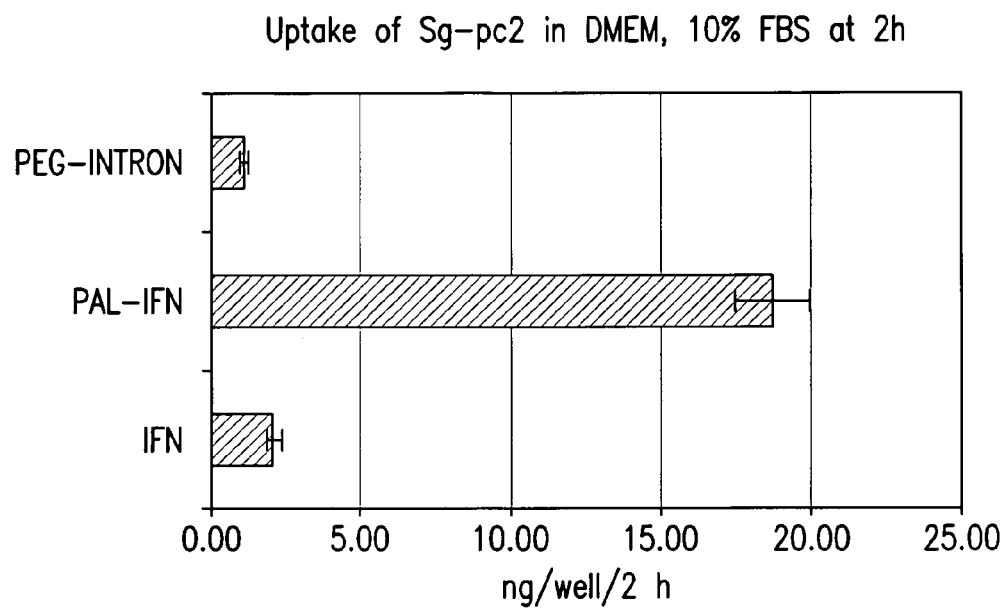
FIGS. 4A and 4B are a graph and bar graph, respectively, which illustrate the uptake of PAL-IFN, IFN and PEG-INTRON in Sg-PC2 cell line and primary cultured mouse hepatocytes.

Sg-PC2 is a human hepatoma cell line, huh-7, transfected with HCV RNA self-replicon. Sg-PC2 was seeded at a density of $2.5 \times 10^5$ per well in a 12-well plate, cultured in DMEM/10% FBS at 37° C. in a humidified 5% $CO_2$ atmosphere until cells reached confluence. The cells were washed once with PBS and then incubated with DMEM/10% FBS containing $^{125}$I-IFN, $^{125}$I-PAL-IFN or $^{125}$I-PEG-INTRON for 2 hours at 37° C. The cells were then trypsinized and harvested for measurement of radioactivity. The results are shown in FIG. 4A. The uptake of PAL-IFN in Sg-PC2 is 17-fold higher than that of PEG-INTRON and 9-fold higher than that of IFN.

Figure 4B:
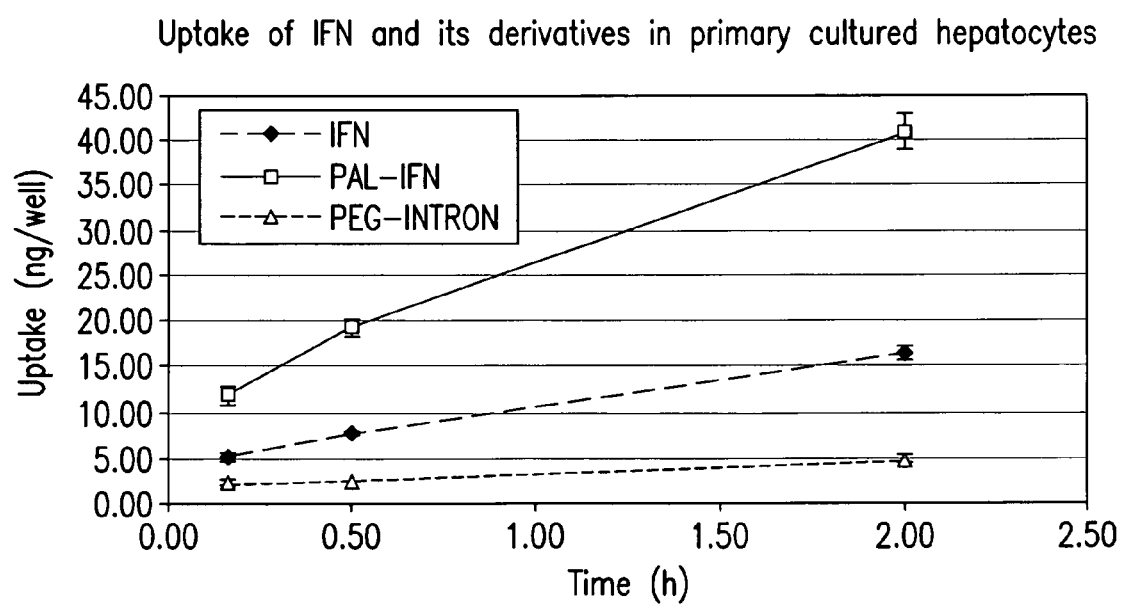

The increased hepatocytic cellular uptake of PAL-IFN was further confirmed in primary cultured mouse hepatocytes. The primary mouse hepatocytes were obtained by the perfusion of collagenase solution to mouse livers. The hepatocytes were seeded in 12-well plates at density of $2.5 \times 10^5$ cells per well, and cultured for 24 hours in DMEM/F12 containing 10% FBS. The cells were then incubated with $^{125}$I-IFN, $^{125}$I-PAL-IFN or $^{125}$I-PEG-INTRON. After incubation for 10 min, 30 min and 2 h, cells were collected for measurement of radioactivity. Data are expressed as the mean of uptake (ng/well)±SD. As shown in FIG. 4B, the uptake of PAL-IFN into the cells increased with prolonged incubation time. At each observed time point, the uptake of PAL-IFN was significantly higher than that of PEG-INTRON or IFN. For example, the PAL-IFN level in cells was 2.5-fold higher than IFN, and 8.6-fold higher than PEG-INTRON at 2 hours post incubation.

Example 6

The Recovery of IFN Activity in Serum Following an iv Injection of PAL-IFN to Mice PAL-IFN or IFN was administered to CF-1 mice through tail veins at a dose of 0.1 mg/kg body weight (BW). Three mice were sacrificed from each experimental group at 10 min, 2, 4 and 8 hours post injection. Blood was collected from the heart and serum was obtained by centrifugation of blood at 6,000 rpm for 30 min after overnight clotting at 4° C.

The IFN activity in serum was quantified using an antiproliferation assay against Daudi cells. Daudi cells were seeded at a density of $2 \times 10^5$ cells/ml in a 96-well plate, and cultured at 37° C. in a humidified 5% $CO_2$ atmosphere. Threefold serial dilutions of serum and IFN standard were added to the cells. After four days, 20 μl of CellTiter 96 Aqueous One Solution Reagent (Promega, Madison, Wis.) was pipetted into each well, and absorbance of 490 nm was recorded to analyze cell proliferation in each well. The amount of serum IFN activity in each well was calculated from the formula generated from the simulation of the corresponding IFN standard curve.

Figure 5:
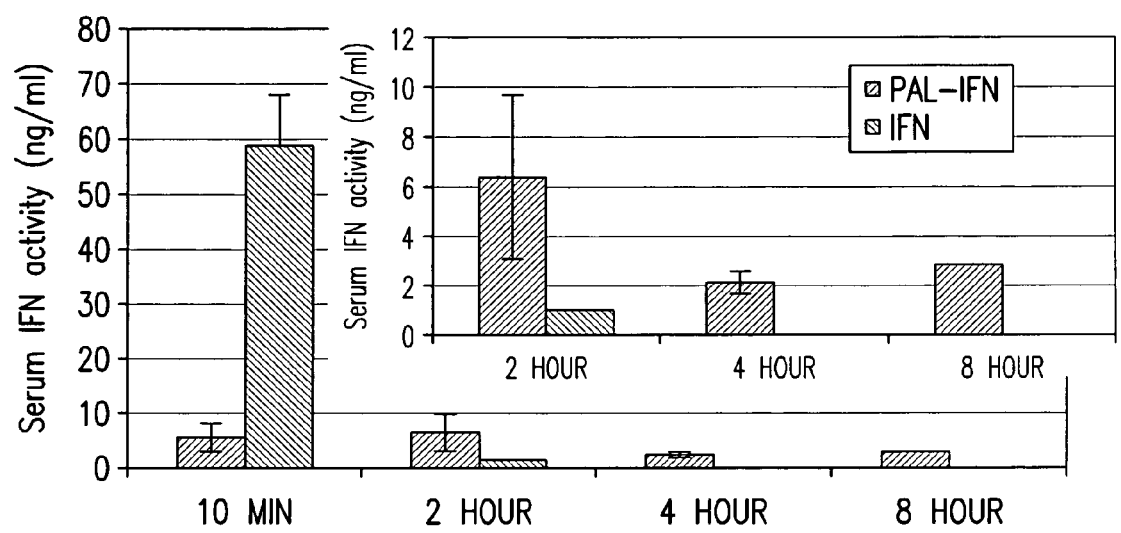
FIG. 5 is a bar graph illustrating the recovery of IFN activity in serum following an intravenous injection of PAL-IFN or IFN to mice.

FIG. 5 shows that the IFN activity was regenerated from PAL-IFN in vivo at a low, but sustained level, for up to 8 h. In comparison, after native IFN was administered to mice, serum IFN activity was rapidly diminished to an undetectable level at 2 h post-injection.

Example 7

Induction of Liver 2',5' Oligoadenylate Synthetase 1 (OAS1) Expression In Vivo

Liver OAS1 expression was used as a surrogate marker of IFN-induced anti-viral activity. CF-1 mice weighing 27-30 g were grouped randomly. Three mice per group were intravenously administered with PBS, 0.2 mg/kg BW of IFN, and 0.2 mg/kg BW of PAL-IFN, respectively. At 24 hours post injection, mice were sacrificed and livers were excised.

A piece of wet liver tissue (0.5 g) was homogenized in 5 ml of modified lysis buffer (50 mM Tris-HCl, 50 mM KCl, 3 mM $Mg(OAc)_2$, 0.3 mM EDTA, 10% glycerol, 0.01% $NaN_3$, 0.5% Triton-X 100, 0.1 mM phenylmethylsulfonyl fluoride (PMSF), 7 mM 2-mercaptoethanol, pH 7.5). The liver homogenates were centrifuged at 20,800×g for 30 min at 4° C. and the supernatants were aliquoted for storage at −80° C. Total protein concentration in the supernatants was determined by the BCA protein assay (Pierce Biotechnology, Rockford, Ill.).

An aliquot of the liver extract (corresponding to 300 μg of wet tissue) was subjected to 12% sodium dodecyl sulfate-polyacrylamide gel electrophoresis (SDS-PAGE), and then transferred to polyvinylidene difluoride (PVDF) membrane by wet blotting at constant 200 mA for 90 minutes. The membrane was blocked in 5% non-fat dry milk at room temperature for 1 hour and then incubated with a rabbit anti-OAS1 polyclonal antibody (Abgent, San Diego, Calif.) with a dilution of 1:500 at 4° C. overnight. The membrane was then washed and incubated with peroxidase-conjugated goat anti-rabbit IgG with a dilution of 1:50,000 for 1 h at room temperature. The signal was detected by incubating the membrane with ECL plus reagents (Amersham Biosciences, Piscataway, N.J.) for 1 min, and exposing the membrane to an X-ray film for 2 min. The density of each lane was quantified by Quantity One software (BioRad, Hercules, Calif.). To normalize the protein loading in each membrane, β-actin was measured after stripping the membrane and re-hybridizing with mouse anti-β-actin monoclonal antibody.

Figure 6A:
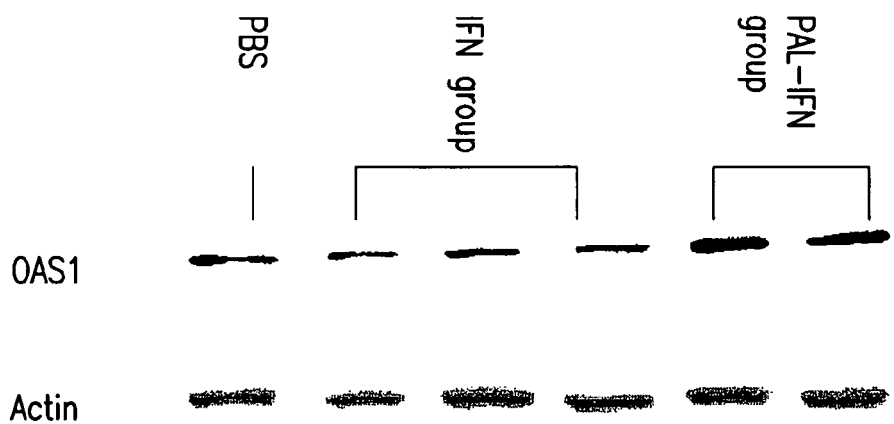
FIGS. 6A and 6B are a Western blotting picture and bar graph, respectively, which illustrate the expression of OAS1 in the liver upon intravenous injection of PAL-IFN or IFN to mice.
Figure 6B:
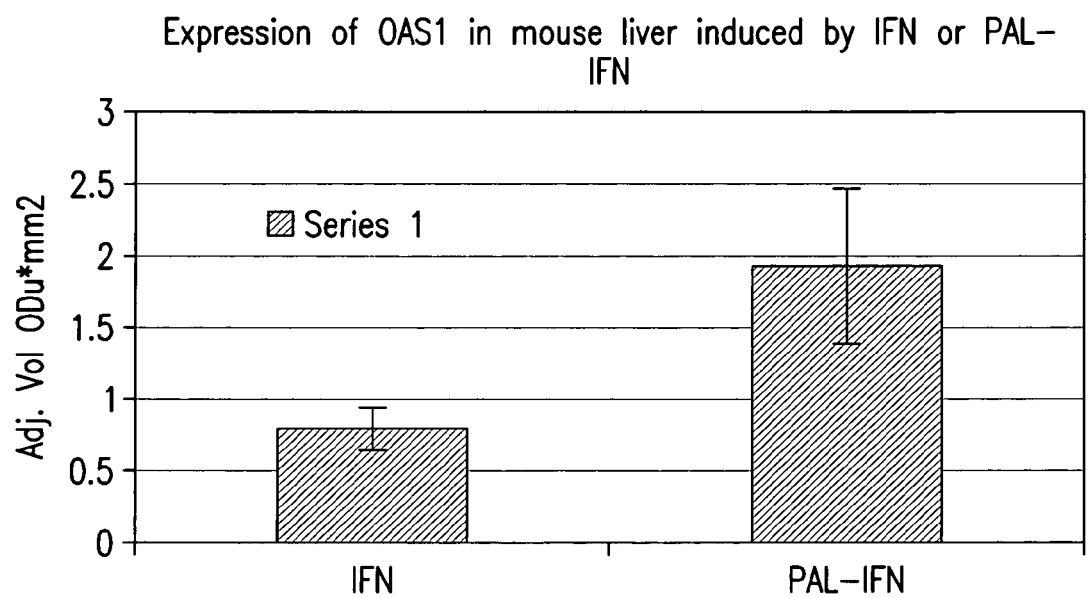

As shown in FIG. 6, treatment with PAL-IFN significantly enhanced the protein level of OAS1 in liver by 2.5-fold, as compared to the treatment with native IFN after 24 hours. OAS1 is a well-defined interferon-induced protein. It catalyzes the synthesis of 2',5'-linked oligoadenylate from ATP, referred to as 2-5A. 2-5A binds and activates ribonuclease L, which cleaves mRNA, leading to the inhibition of viral replication. OAS1 induction is directly associated with the antiviral efficacy of IFN. Therefore, increased expression of OAS1 locally in liver would significantly enhance the therapeutic efficacy of PAL-IFN against viral hepatitis.

Example 8

Characterization of PAL-IFN with Far-UV Circular Dichroism (CD)

PAL-IFN and IFN were eluted and collected from HPLC. To obtain Far-UV CD spectra, 1 uM of PAL-IFN in 50% acetonitrile/0.1% TFA was loaded into a cuvette with 1.0 cm path-length. The cuvette was positioned in a Jasco J810 Spectropolarimeter (Jasco Inc, Easton, Md.). Complete spectra were collected at room temperature with 100 scans in the wavelength range of 190-260 nm. IFN and buffer (50% acetonitrile/0.1% TFA) spectra were collected in the same condition. PAL-IFN and IFN spectra were subtracted from buffer spectra. The final spectra data were analyzed using Origin 7 software (OriginLab Corporation, Northampton, Mass.).

Figure 7:
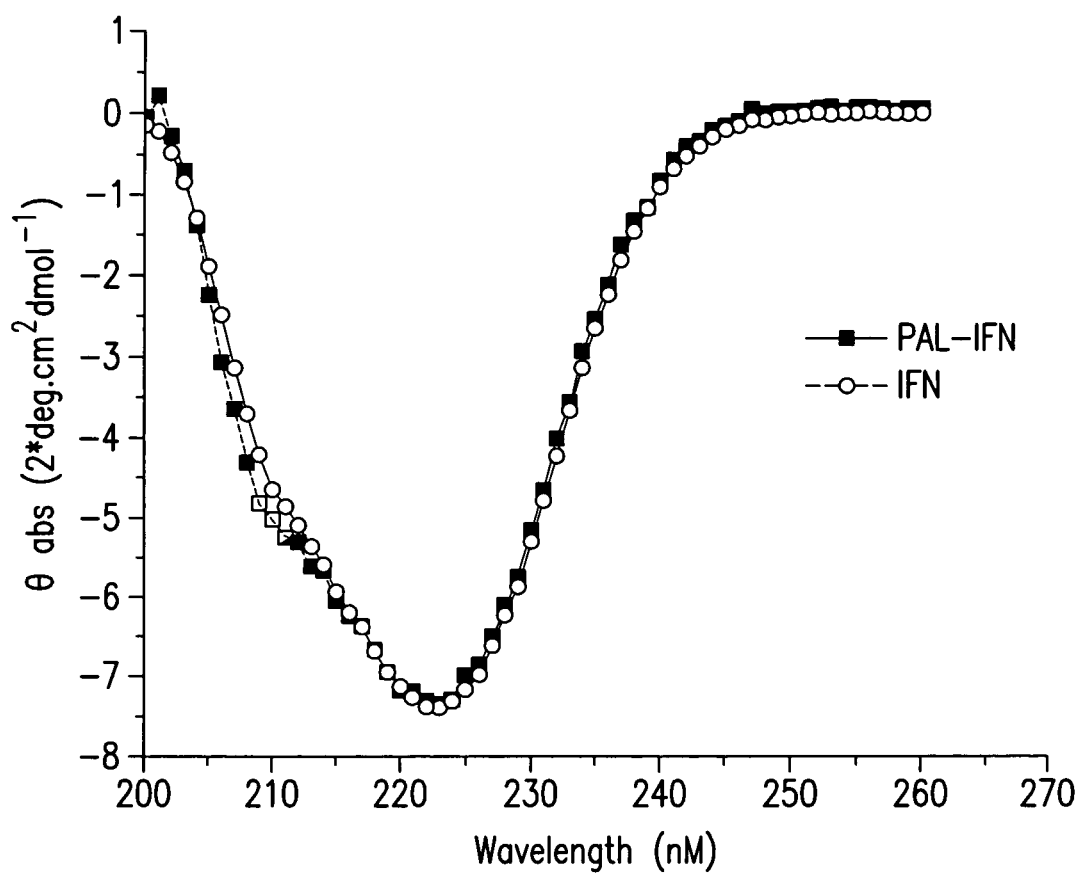
FIG. 7 is a circular dichroism plot illustrating the similar structures of PAL-IFN and IFN.

As shown in FIG. 7, the CD spectra of PAL-IFN are virtually overlapped with that of IFN, which indicates that PAL-IFN maintains a structure close to native IFN. The deep peak at 222 nm indicates that both PAL-IFN and IFN comprise mainly alpha helices.

Having now fully described the invention, it will be understood by those of ordinary skill in the art that the same can be performed within a wide and equivalent range of conditions, formulations and other parameters without affecting the scope of the invention or any embodiment thereof. All patents, patent applications and publications cited herein are fully incorporated by reference herein in their entirety.

What is claimed is:

1. An isolated homogenously modified polypeptide consisting essentially of interferon-α reversibly conjugated with a first palmitoyl cysteine at a first cysteine residue, a second palmitoyl cysteine at a second cysteine residue, a third palmitoyl cysteine at a third cysteine residue and a fourth palmitoyl cysteine at a fourth cysteine residue.

2. The polypeptide of claim 1, wherein said interferon-α is human interferon-α.

3. The polypeptide of claim 2, wherein the palmitoyl cysteine is conjugated to Cys1, Cys29, Cys98, and Cys138.

4. A pharmaceutical composition comprising the polypeptide of claim 1.

5. A method of treating viral hepatitis in a subject, comprising administering to said subject an effective amount of the polypeptide of claim 1.

6. A method for increasing liver uptake of interferon-α upon administration to a subject, comprising administering the polypeptide of claim 1 to said subject.

\* \* \* \* \*

UNITED STATES PATENT AND TRADEMARK OFFICE
CERTIFICATE OF CORRECTION

PATENT NO.      : 8,486,384 B2
APPLICATION NO. : 12/446487
DATED           : July 16, 2013
INVENTOR(S)     : Shen et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 116 days.

Signed and Sealed this
Eighth Day of September, 2015

Michelle K. Lee
*Director of the United States Patent and Trademark Office*